United States Patent [19]

Jang

[11] Patent Number: 5,611,806
[45] Date of Patent: Mar. 18, 1997

[54] SKIN PERFORATING DEVICE FOR TRANSDERMAL MEDICATION

[75] Inventor: Kwang K. Jang, Kyungki-Do, Rep. of Korea

[73] Assignee: Samsung Electro-Mechanics Co., Ltd., Kyungki-do, Rep. of Korea

[21] Appl. No.: 450,949

[22] Filed: May 23, 1995

[30] Foreign Application Priority Data

May 23, 1994 [KR] Rep. of Korea .................. U94-11522
May 23, 1994 [KR] Rep. of Korea .................. U94-11523

[51] Int. Cl.⁶ .................................................. A61B 17/32
[52] U.S. Cl. ........................ 606/167; 606/189; 606/133
[58] Field of Search ................................. 606/180, 132, 606/167, 133, 189, 131

[56] References Cited

U.S. PATENT DOCUMENTS 5,171,315  12/1992  Cabrero ............................. 606/133

FOREIGN PATENT DOCUMENTS 0752284  4/1966  Italy ................................. 606/189
92-2264  3/1992  Rep. of Korea .
1641346  4/1991  U.S.S.R. ........................... 606/189

OTHER PUBLICATIONS

Korean Patent Application No. 93-21511, Oct. 16, 1993.
Korean Patent Application No. 93-21512, Oct. 16, 1993.
Korean Patent Application No. 93-21513, Oct. 16, 1993.

Primary Examiner—Michael Powell Buiz
Assistant Examiner—Kevin Truong
Attorney, Agent, or Firm—Lowe, Price, LeBlanc & Becker

[57] ABSTRACT

A skin perforating device comprises a plurality of alternately disposed needle disks and spacers which are combined together for rotational movement as a unit. Attached to the opposite ends of the device are a pair of end plates whose diameter is greater than that of the spacers. The end plates enable the skin perforating device to create skin cuts of uniform depth throughout the length thereof, thus avoiding pain and flare which would occur in the absence of the end plates. Each of the needle disks is provided with a multiplicity of skin perforation needles on its circumference. The skin perforation needles are of triangular configuration and have lateral sides of acute wave form such that the bodily skin can be cut readily by the skin perforation needles thereof.

10 Claims, 4 Drawing Sheets

SKIN PERFORATING DEVICE FOR TRANSDERMAL MEDICATION

FIELD OF THE INVENTION

The present invention relates to the forming of minute cuts on bodily skin for the transdermal delivery of liquid or gel-like drugs. More particularly, the present invention relates to a skin perforating device to facilitate delivery of transdermal medication which includes a plurality of alternately disposed needle disks and spacers, each needle disk having skin perforation needles of triangular configuration on its circumference to leave drug delivery cuts in a uniform depth over the full span of a treatment region of the skin, with the triangular needles assuring an optimized skin cutting operation.

DESCRIPTION OF THE PRIOR ART

As is generally known in the art, insulin works well in the medical treatment of diabetic patients and is composed of macromolecules whose molecular weight it more than 6,000. Due to their size, insulin molecules have difficulty penetrating the skin of diabetics even if the skin is properly treated with a chemical solvent. More importantly, insulin, as a peptide combination of amino acids, is a highly hydrophillic drug having little affinity with the skin which is intrinsically hydrophobic. The inability of insulin to penetrate skin tends to make transdermal administration a less suitable mode of delivery.

Anatomically, the skin of a human body can be subdivided into an epidermis, a dermis and an endodermis, among which the epidermis plays a key role in making transdermal drug delivery difficult. The epidermis is 0.1 mm or more in thickness and consists of about 20% lipid and about 40% protein among other things. Each segment of the protein is surrounded by lipid, thus rendering the epidermis hydrophobic. As compared with the water content of the dermis and the endodermis that reaches more than 70%, the epidermis contains no more than 40% water. Accordingly, the epidermis has a tendency to exhibit an increased electrical resistance and serves to protect the dermis and the endodermis from thermal attack or similar external stimuli.

Prior art techniques of applying insulin through the skin include ointments, patches and sprays. In recent years, patch-type transdermal techniques for delivery of insulin has been the frequent subject of research and development.

Korean Patent Publication No. 92-2264 discloses a patch-type device for transdermelly delivering insulin to patients. As illustrated in FIG. 1, the insulin delivery device comprises an insulin solvent reservoir 1 constituting a framework of the device, a water-swellable, high molecular, insulin-carrying layer 2 on which insulin is dispersed in a powder form, a needle support 3 adapted to expand as the insulin solvent is discharged from the reservoir 1, a multiplicity of skin perforation needles 4 extending vertically from the needle support 3 so as to come into contact with the bodily skin and an electrode 5 attached to the ceiling of the reservoir 1 for supplying the reservoir 1 and the bodily skin with electricity.

In accordance with the above-referenced insulin delivery device, the skin perforation needles 4 create passageways when they are pressed against the skin. The passageways will temporarily close due mainly to the swelling of the perforated skin. Application of direct current or alternating current to the electrode 5 housed within reservoir 1 will cause ionized insulin and solvent to move toward the opposite electrode, in which event, the hydrophilic protein and polypeptide of the skin would be arranged in parallel to the anode, thereby resulting in shrinkage of the skin and hence enlargement of the passageways. This eventually allows insulin to penetrate into the hypodermis. The reason for employing a multiplicity of skin perforation needles 4 in the device noted above is to painlessly perforate the epidermis which exceeds 0.1 mm in thickness, assuring an enhanced delivery of insulin into capillary vessels through the dermis and the endodermis.

As is apparent from the foregoing, the needle support in the prior art device is designed to carry, as a unit, tens or hundreds of skin perforation needles on the surface thereof, making it difficult to shape the needles to have a diameter of 50–400 μm. The needle support which exhibits swelling behavior in response to the discharge of insulin solvent is costly to manufacture. Since the needle support has to be built in the reservoir inseparably, it is not possible to re-use the needle support, which increases the financial burden borne by the patient.

Moreover, despite the fact that the number of skin perforation needles should ideally number in more than thousands in order to expedite insulin delivery, the conventional insulin patch device makes use of only tens or hundreds of needles, thus retarding the delivery rate of insulin through the skin. As a result, the diabetic patient has to wear the insulin patch for an extended period of time, which is painful and inconvenient.

As an alternative, there is taught in Korean Patent Application Nos. 93-21511, 21512 and 21513 a skin pretreatment device that includes a needle plate and thousands of skin perforation needles fixedly attached to the needle plate in a substantially uniform pattern. The skin pretreatment device is capable of creating thousands of fine cuts simply by way of pressing the needle plate against the surface of skin without having to use a separate driving apparatus.

With the skin pretreatment device referred to just above, it is difficult, if not impossible, to provide thousands of skin perforation needles on a small-size needle plate even with state-of-the-art technology. In other words, the skin pretreatment device has proven to pose several drawbacks in terms of workmanship, productivity and practical usability.

SUMMARY OF THE INVENTION

It is an object of the invention to provide a skin perforating device for transdermal delivery of medication which can eliminate the drawbackss inherent in the prior art device and which has the ability to introduce drug delivery perforations of uniform depth on a bodily skin with no or little pain and flare during and after the introduction of the drug delivery perforations.

Another object of the invention is to provide a skin perforating device for transdermal medication capable of increasing the effective area of cuts to be formed in a specific medical treatment zone of the bodily skin and consequently expediting drug delivery through the cuts.

With these objects in view, the present invention provides a skin perforating device comprising a plurality of needle disks having skin perforation needles on their circumferential formed thereon and a central shaft for holding the needle disks assembled therealong in a face-to-face relationship with one another. It is preferred that the skin perforation needles are of triangular shape and have lateral sides of acute wave form. Moreover, the skin perforation needles in each of the needle disks should preferably be spaced apart at an equal pitch with the individual needle disks so combined that the skin perforation needles in one needle disk remain staggered from those of the adjoining needle disk.

BRIEF DESCRIPTION OF THE DRAWINGS

The above and other objects, features and advantages of the invention will become apparent from a review of the following description of the preferred embodiments taken in conjunction with the accompanying drawings, in which.

DESCRIPTION OF THE PREFERRED EMBODIMENTS

Figure 1:
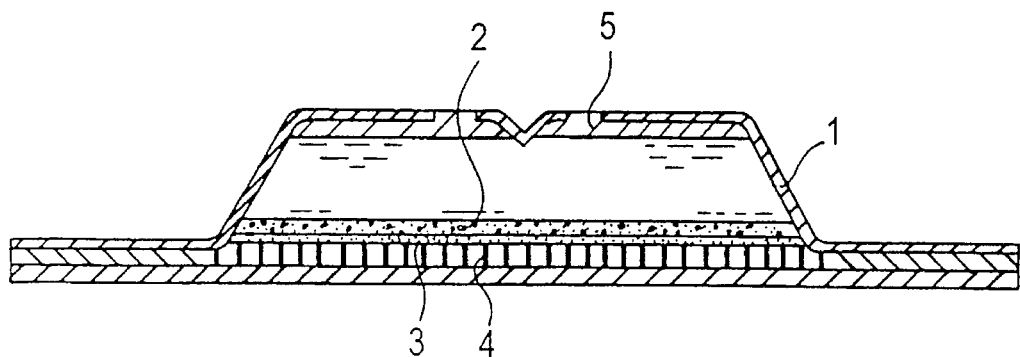
FIG. 1 is a sectional view of a prior art transdermal insulin delivery pitch.
Figure 2:
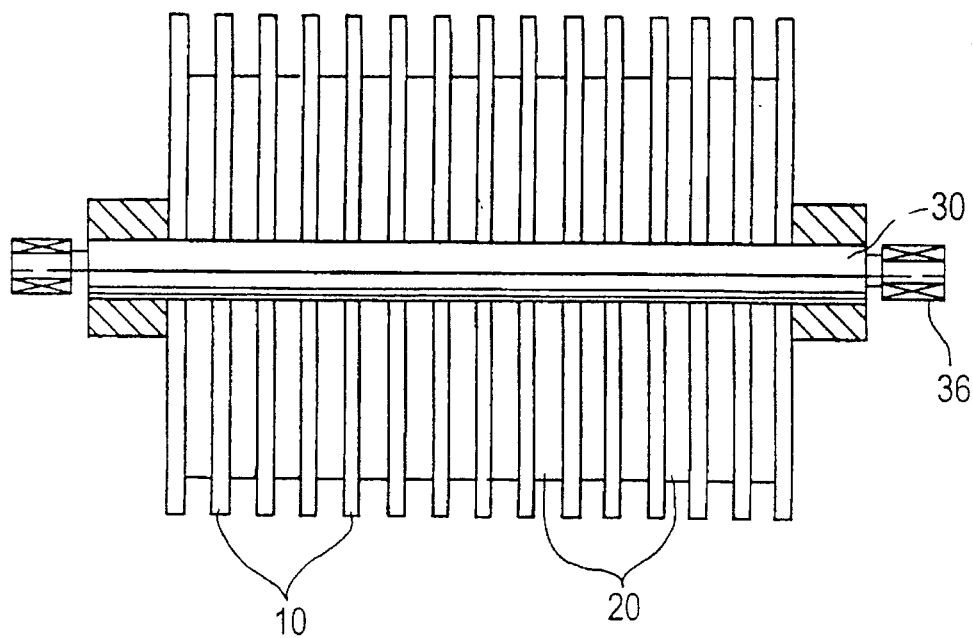
FIG. 2 is a partially sectional, front view of the skin perforating device for transdermal medication in accordance with a first embodiment of the invention.

Referring now to FIGS. 2 through 5, first embodiment of the skin perforating device comprises a plurality of needle disks 10 that have tens or hundreds of skin perforation needles 12 formed in a consistent spacing along the circumferential surfaces of the needle disks. The needle disks 10 each have an axial hole 14 through which a central shaft 30 is inserted snugly and a number of (e.g., four) offset holes 16 through which peripheral bars 32 are adapted to pass. It should be appreciated that the skin perforation needles 12 can be produced by virtue of etching, press work or other suitable techniques.

Alternately disposed between the needle disks 10 are a plurality of disk-like spacers 20 which serve to keep the needle disk 10 spaced apart from one another. Each of the spacers 20 has an axial hole 22 and offset holes 24 that corresponds respectively to the axial hole 14 and the offset holes 16 (FIG. 3 only) of the needle disks 10. If desired, the spacers 20 may be integrally formed with the needle disks 10.

At the opposite ends of the skin perforating device, a pair of end plates 34 are attached in close contact with the outermost needle disks 10. The central shaft 30 that passes through the axial holes 14, 22 allows the skin perforating device to rotate thereabout, while the peripheral bars 32 that extends through the offset holes 16, 24 parallel to the central shaft 30 function to combine the needle disks 10 and the spacers 20 together in a stacked condition.

Bearings 36 are fitted to the opposite ends of the central shaft 30 to make the skin perforating device freely rotatable when carried by a handle (which is not shown in the drawings for simplicity).

The skin perforating device of the construction set forth above can be fabricated by way of alternately stacking the needle disks 10 and the spacers 20 so that the axial holes 14, 22 and the offset holes 16, 24 may respectively coincide with each other, inserting the central shaft 30 and the peripheral bars 32 through the axial holes 14, 22 and the offset holes 16, 24, respectively, and tightening nuts on the terminal ends of each of the central shaft 30 and the peripheral bars 32. In this process of fabrication, the central shaft 30 should be fixedly secured to the needle disks 10 by caulking or other suitable fastening means. As with the conventional paint application roller, a handle may be attached to the ends of the central shaft 30 to thereby enable the skin perforating device to be rotatable about the central shaft 30 as the skin perforation work proceeds.

When in use, the skin perforation device is pressed against the skin so that the skin perforation needles 12 can contact the skin region which is to be subjected to perforation. The skin perforation device is subsequently caused to rotate about the central shaft 30 to leave a multiplicity of fine cuts on the pretreatment region of the skin. An insulin patch will be placed upon the pretreatment region to allow insulin to be transdermally delivered through the fine skin cuts.

Figure 3:
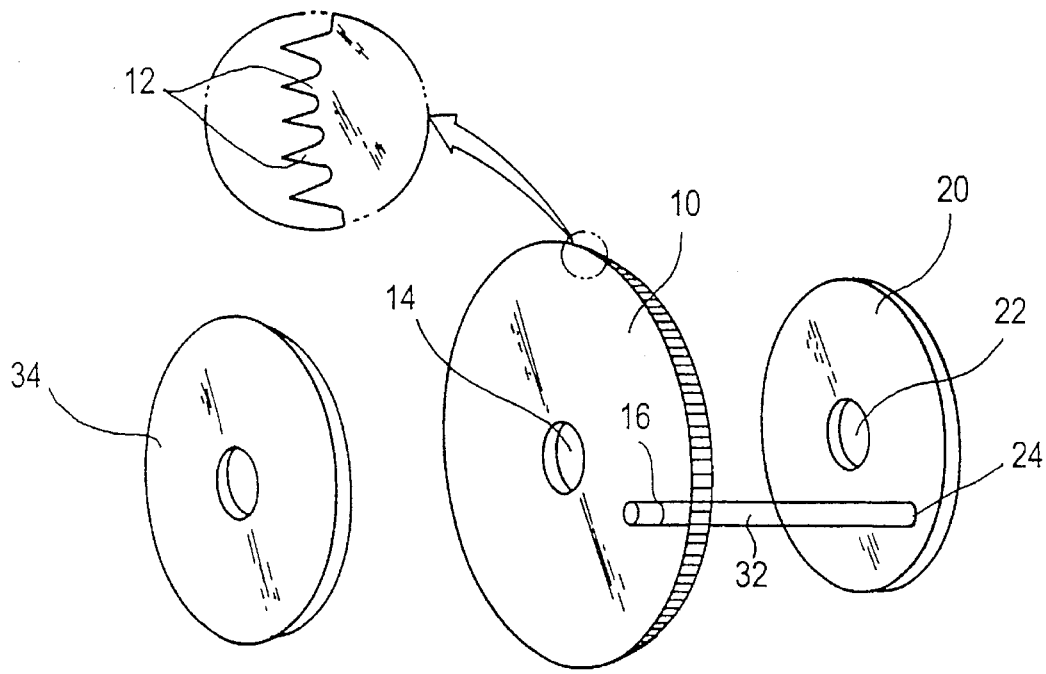
FIG. 3 is an exploded perspective view of the needle disk and spacers employed in the instant skin perforating device.
Figure 4:
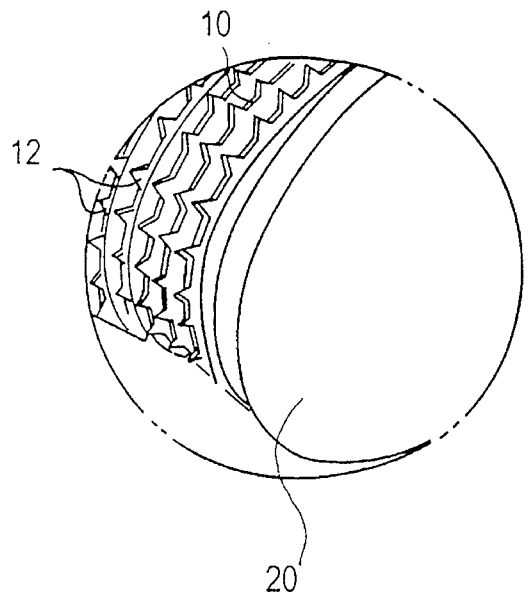
FIG. 4 is a perspective view showing a major portion of the components illustrated in FIG. 2 on an enlarged scale.
Figure 5:
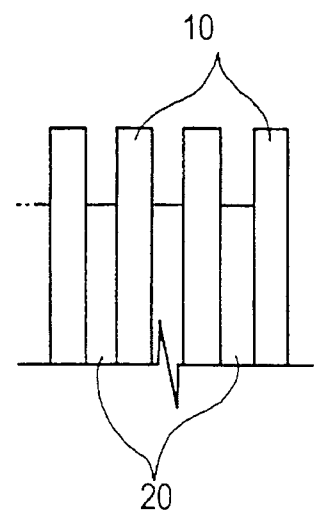
FIG. 5 is a partially enlarged view illustrating the needle disk assembly shown in FIG. 2.

As best shown in FIG. 3, the end plates 34 employed in the skin perforating device of the first embodiment have a diameter far smaller than that of the needle disks 10. For the very reason, the skin perforation needles 12 of the outermost needle disks 10 may penetrate into the skin to a greater depth than the needles of the remaining needle disks, sometimes causing the user to suffer pain and flare.

Figure 6:
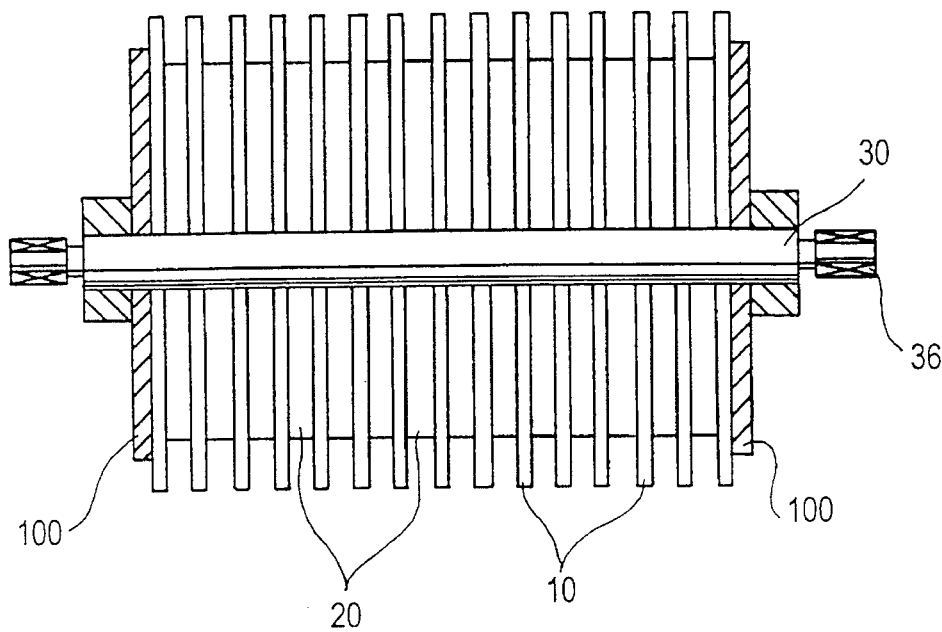
FIG. 6 is a partially sectional, front view of the skin perforating device for transdermal medication in accordance with the second embodiment of a invention.
Figure 7:
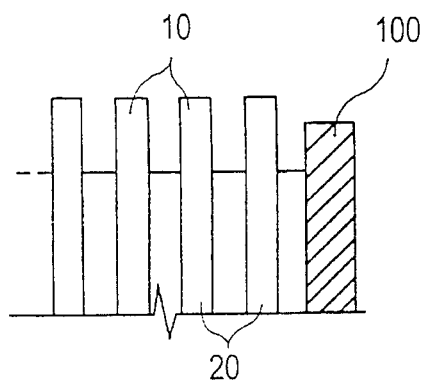
FIG. 7 is a partially enlarged view illustrating a portion of the skin perforating device shown in FIG. 6.

Such a shortcoming posed in the above-noted skin perforating device can be ameliorate by use of the skin perforating device shown in FIGS. 6 and 7 wherein a particular reference numeral designates like parts or components.

Referring collectively to FIGS. 6 and 7, it can be seen that the needle disks 10 and the spacers 20 are alternately stacked along their rotational axis with end plates 100 attached to each of the outermost spacers 20. The end plates 100 have an important feature that the diameter thereof is greater than that of the spacers 20. This will help prevent the outermost needle disks 10 from creating overly deep cuts. More specifically, the end plates 100 serve as a guide when the skin perforating device is rolling on the surface of the bodily skin, thus ensuring that the depth of skin cuts is uniform throughout the width of the perforation region, which would otherwise cause pain. It is preferred that each of the end plates 100 is a disk-like configuration and has a diameter which is equal to the "pitch circle" of the needle disks 10 or greater than the "root circle" thereof.

As may be seen in FIG. 3, the skin perforating device of the foregoing embodiments is provided with skin perforation needles of simple triangular geometry which may be less effective in creating the skin cuts of desired depth and width. Accordingly, a need exists for a needle disk having skin perforation needles with an improved configuration.

Figure 8:
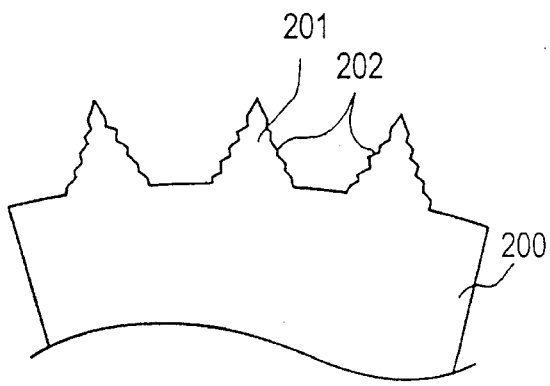
FIG. 8 is a partially enlarged view showing a needle disk that constitutes the skin perforating device in accordance with the third embodiment of a invention.

Turning now to FIG. 8, there is illustrated a needle disk 200 adapted for use in the skin perforating device in accordance with the third embodiment of the invention. As shown, the needle disk 200 is modified to have skin perforation needles 201 whose lateral sides 202 are each formed with a plurality of teeth (e.g. of sawtooth configuration as depicted in FIG. 8). By using the needle disk 200 illustrated in FIG. 8, it becomes possible to broaden the contact area of the needles with the bodily skin, thus leaving wide skin cuts that can facilitate drug delivery therethrough. This will help shorten the time period of applying drugs to the user of the inventive skin perforating device.

Figure 9:
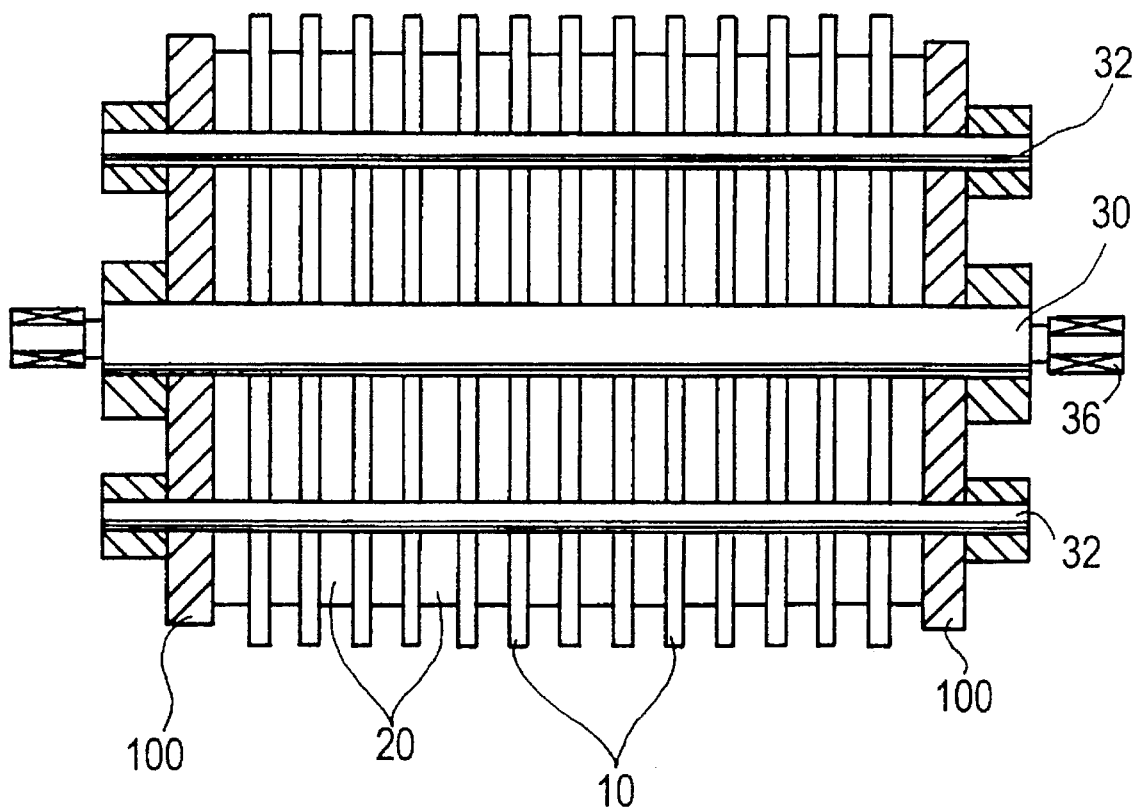
FIG. 9 is a front elevational view of the skin perforating device in accordance with the third embodiment of the invention.

Referring to FIG. 9, there is shown, in assembly, the skin perforating device associated with the third embodiment of the invention. In this embodiment, the skin perforating device comprises a plurality of alternately disposed needle disks 10 and spacers 20, a pair of end plates 100 attached to the opposite ends of the device, a central shaft 30 inserted into the axial hole of the needle disks 10 and the spacers 20 and a plurality of peripheral bars 32 which are offset radially outwards from the central shaft 30. The skin perforating device of the third embodiment is distinguishable over the preceding embodiments in the shape of skin perforation needles formed around the needle disks 10.

As set forth in detail hereinabove, the inventive skin perforating device is able to leave skin cuts of uniform depth without any fear of pain and flare. Furthermore, thanks to the irregularly shaped needles, the skin perforating device can produce skin cuts of increased effective area which leads to an expedited drug delivery.

While the invention has been described with reference to certain preferred embodiments it should be apparent to those skilled in the art that many changes and modifications may be made without departing from the spirit and scope of the invention as defined in the claims.

What is claimed is:

1. A skin perforating device for forming a plurality of drug delivery cuts in bodily skin to facilitate delivery of transdermal medication, comprising:

a plurality of needle disks each having a plurality of circumferentially spaced skin perforation needles;

a central shaft for holding the needle disks in assembled relation therealong in a face-to-face relationship with one another;

a plurality of spacers assembled on the central shaft in alternately disposed relationship between substantially each of the needle disks;

a pair of end plates assembled at opposite ends of the central shaft, respectively, an outer diameter of each end plate being greater than a first diameter of the needle disks measured at a point from which a base of each needle extends radially from the disk and less than a second diameter as measured from the needle tips; and fixing means for fixing and joining the needle disks, spacers and end plates together on the central shaft.

2. The skin perforating device as recited in claim 1, wherein each of the skin perforation needles of the needle disks is of generally triangular shape and is formed with saw-teeth on peripheral triangular sides thereof.

3. The skin perforating device as recited in claim 1, wherein the skin perforation needles on each respective needle disk are spaced apart at a uniform pitch.

4. The skin perforating device as recited in claim 1, wherein the fixing means is locked onto the central shaft.

5. The skin perforating device as recited in claim 1, wherein the skin perforation needles on one needle disk are staggered with respect to those of the immediately adjoining needle disk.

6. The skin perforating device as recited in claim 1, wherein the peripheries of the end plates are round.

7. The skin perforating device as recited in claim 1, wherein the fixing means comprises fixing members which are fixedly disposed at opposite ends of the central shaft, respectively.

8. The skin perforating device of claim 1, wherein each needle disk is substantially flat and opposing sides of each disk are substantially coplanar with corresponding opposing sides of the needle teeth projecting from the associated disk.

9. A skin perforating device for forming a plurality of drug delivery cuts in bodily skin to facilitate delivery of transdermal medication, comprising:

a plurality of needle disks each having a plurality of circumferentially spaced skin perforation needles arranged in a single plane, said needles having opposed flat faces which are respectively coplanar with opposing flat faces of the associated disk;

a plurality of spacers in alternately disposed relationship between substantially each of the needle disks; and means for fixing the needle disks and spacers together in assembled relation.

10. The skin perforating device of claim 9, wherein each needle has a pair of sides intersecting each other to form a triangle projecting radially outward from the associated disk, each side being formed with a plurality of jagged edges or teeth to facilitate the formation of drug delivery cuts in said bodily skin.

\* \* \* \* \*